(12) United States Patent
Lin

(10) Patent No.: US 8,784,905 B2
(45) Date of Patent: Jul. 22, 2014

(54) OIL-EXTRACTED PRODUCT OF INDIGO NATURALIS, AND PREPARATION PROCESS AND USES THEREOF

(75) Inventor: Yin-Ku Lin, Taipei (TW)

(73) Assignee: Galderma Research & Development, S.N.C., Valbonne (FR)

( * ) Notice: Subject to any disclaimer, the term of this patent is extended or adjusted under 35 U.S.C. 154(b) by 181 days.

(21) Appl. No.: 13/274,506

(22) Filed: Oct. 17, 2011

(65) Prior Publication Data

US 2012/0213868 A1 Aug. 23, 2012

(30) Foreign Application Priority Data

Feb. 18, 2011 (TW) .............................. 100105463 A

(51) Int. Cl.
*A61K 36/195* (2006.01)
(52) U.S. Cl.
USPC .......................................... 424/725; 424/401

(58) Field of Classification Search
CPC ..... A61K 36/195; A61K 36/704; A61K 8/92; A61K 8/922; A61K 8/925
USPC ................................................... 424/725, 401
See application file for complete search history.

(56) References Cited

FOREIGN PATENT DOCUMENTS

CN 1019546 B * 12/1992
JP 2006-111793 A * 4/2006

OTHER PUBLICATIONS

Handa, ed. (Extraction Technologies for Medicinal and Aromatic Plants. Italy: ICS-UNIDO. 2008. pp. 32 and 33).*

* cited by examiner

*Primary Examiner* — Susan Hoffman
(74) *Attorney, Agent, or Firm* — Nath, Goldberg & Meyer; Joshua B. Goldberg

(57) ABSTRACT

Disclosed herein are an oil-extracted product of indigo naturalis, and the preparation process thereof. Also disclosed are a pharmaceutical composition containing the oil-extracted product of indigo naturalis and a method for treating a human subject having or suspected to have a psoriatic disease such as skin psoriasis and nail psoriasis.

14 Claims, 4 Drawing Sheets

OIL-EXTRACTED PRODUCT OF INDIGO NATURALIS, AND PREPARATION PROCESS AND USES THEREOF

CROSS-REFERENCE TO RELATED APPLICATIONS

This application claims priority of Taiwanese Application No. 100105463, filed on Feb. 18, 2011.

BACKGROUND OF THE INVENTION

1. Field of the Invention

This invention relates to an oil-extracted product of indigo naturalis and a process for preparing the same. This invention also relates to a pharmaceutical composition comprising said oil-extracted product, and a method for treating psoriasis, in particular skin psoriasis and nail psoriasis, in which the use of said oil-extracted product is involved therein.

2. Description of the Related Art

Psoriasis is a chronic inflammatory skin disease that may appear on the skin at any area of the body, in particular head, limbs, elbows, knees, etc. Red papules or plaques having clear borders are frequently observed on the skins of psoriasis patients, and the surfaces of the skin lesions of the patients may be covered by silvery-white scales. Some psoriasis patients may even develop arthritis or other symptoms at the same time.

According to skin symptoms, psoriasis is clinically classified into the following four types: chronic plaque psoriasis, guttate psoriasis, erythrodermic psoriasis, and pustular psoriasis. Chronic plaque psoriasis, also known as vulgaris psoriasis, is most commonly seen amongst all the types of psoriasis, and around 80%-90% of psoriasis patients belong to this type. Guttate psoriasis is characterized by numerous small pink or red teardrop-shaped lesions on patients' skins and usually occurs in children from age 7 to age 10, in which most of the patients are found to have suffered a streptococcal infection one or two weeks before the onset of the disease. Erythrodermic psoriasis is characterized by the appearance of erythema or exfoliation over the whole body's surface or more than 90% of the body's surface, and under more severe conditions, the occurrence of itching over the whole body, which may be further accompanied by fever and malaise. Moreover, generalized acute pustular psoriasis may even be induced in patients with erythrodermic psoriasis. Pustular psoriasis can be further categorized into generalized pustular psoriasis and localized pustular psoriasis (e.g., pustulosis palmaris et plantaris and acrodermatitis perstans). Besides, around 10% of the psoriasis patients have a complication of psoriatic arthritis, which is a CD8 T cell-driven autoimmune inflammatory disorder that affects ligaments, tendons, fascia, and spinal or peripheral joints, while up to 90% of the patients have suffered nail psoriasis.

Due to the complicated pathological conditions and symptoms involved therein, the pathogenesis of psoriasis has yet to be well understood to date. Some studies have revealed that inheritance plays an important role in the pathogenesis of psoriasis, and trauma, infection, stress, endocrine factors, metabolism factors, weather and medication may induce or aggravate psoriasis. After the onset of psoriasis, this disease may recur repeatedly over patients' lifetime and no eradication of the same is possible.

The conventional treatments for psoriasis are generally designed according to the age, gender, occupation and cognitive ability of the patient, the types and distribution of lesions, patient's response(s) to previous therapeutic method(s), and other medical histories of the patient. The primary therapeutic methods for psoriasis include topical therapy, systemic therapy, injection of biologics and phototherapy. Compositions for topical therapy include, e.g., corticosteroids, anthralin (available as Margiton®), coal tar (available as Polytar®), calcitriol (available as Silkis®), tazarotene (available as Tazorac®), salicylic acid, etc., and these compositions are suitable for treating psoriasis patients with mild symptoms. Oral preparations of methotrexate (MTX), cyclosporine, retinoids, etc., are commonly used for systemic therapy and are suitable for treating psoriasis patients with medium to severe symptoms. Biologics include alefacept (available as Amevive®), efalizumab (available as Raptiva®), etanercept (available as Enbrel®) and adalimumab (available as Humira®), and they are suited for injecting into psoriasis patients with medium to severe symptoms. Phototherapy, e.g., ultraviolet B (UVB) phototherapy, photochemotherapy such as psoralen plus ultraviolet A (PUVA), etc., is suitable for treating psoriasis patients with severe symptoms.

However, long-term use of the conventional treatments described above may result in serious side effects or drug tolerance, thereby further reducing patient compliance. In view of the foregoing, many researchers have attempted to explore, from traditional Chinese medicines (TCM), active components that can be used to treat psoriasis.

Indigo naturalis (also referred to as natural indigo; Chinese: Quing dai) is a dark-blue plant pigment extracted from leaves of an indigo-producing plant such as *Baphicacanthus cusia* (Nees) Bremek., *Polygonum tinctorium* Lour., *Isatis indigotica* Fort., etc. Indigo naturalis is known in TCM to have heat-clearing and blood-cooling effect, and it has been clinically used to treat chronic myeloid leukemia, psoriasis, mumps, various ulcers (e.g., peptic ulcers, oral ulcers, etc.), hepatitis, herpes zoster and otitis externa.

It has been known that various active components can be isolated from indigo naturalis prepared from different indigo-producing plants, amongst which the most common active components are indigo, indirubin, isoindigo, etc. It has been reported that indirubin has anti-tumor, anti-inflammation, and immunomodulatory effects and has been considered to have potential in the treatment of chronic myelocytic leukemia (G. Eisenbrand et al. (2000), *J. Cancer Res. Clin. Oncol.*, 130:627-635; T. Kunikata et al. (2000), *European Journal of Pharmacology*, 410:93-100; N. K. Mak et al. (2004), *Biochemical Pharmacology*, 67:167-174; S. Leclerc et al. (2001), *The Journal of biological Chemistry*, 276:251-260).

Indigo naturalis has been reported to have poor water solubility and, hence, not a few researchers have aimed at extracting the active components contained therein using organic solvents. Q. S. Zhang et al. used four different organic solvents, i.e., 75% ethanol, chloroform, ethyl acetate and acetone to extract indigo naturalis, with/without a preliminary 36% HCl treatment, and the indirubin contents of the products thus obtained were determined and compared. The obtained experimental results reveal that regardless of being subjected to the preliminary 36% $HCl_{(aq)}$ treatment or not, the ethyl acetate-extracted product has a highest indirubin content, followed by the acetone-extracted product, the chloroform-extracted product and the 75% ethanol-extracted product. Besides, the preliminary 36% $HCl_{(aq)}$ treatment significantly increases the indirubin content in each organic solvent-extracted product (Q. S. Zhang et al. (2006), *Journal Guangxi Normal University: Natural Science Edition*, 24(3): 58-60).

In previous studies, the applicants developed an indigo naturalis composite ointment formulated by 20% (by weight) indigo naturalis powder and 80% vehicle (containing 25%

Vaseline, 30% yellow wax and 45% olive oil), and investigated the use of said ointment as a topical treatment for psoriasis. The applicants found that topical application of said ointment was effective in treating pediatric psoriasis, recalcitrant psoriasis and plaque-type psoriasis (Y. K. Lin et al. (2006a), *Pediatric Dermatology*, 23(5):507-510; Y. K. Lin et al. (2006b), *Clinical and Experimental Dermatology*, 99-100; and Y. K. Lin et al. (2007), *Dermatology*, 214:155-161).

In a subsequent study, the applicants used an indigo naturalis ointment formulated by indigo naturalis powder and the vehicle described above at a ratio of 1:10 (by weight) to treat outpatients with chronic plaque psoriasis and found that topical application of said ointment resulted in significant reductions in the scaling, erythema and induration scores as well as plaque area percentage (Y. K. Lin et al. (2008), *Arch Dermatology*, 144(11):1457-1464).

The applicants further investigated the anti-psoriatic effect of indigo naturalis on the proliferation and differentiation of keratinocytes, in which an indigo naturalis sample, which was obtained by dissolving indigo naturalis powder in dimethylsulfoxide (DMSO) in a proportion of 1:10 (w/v), followed by sterilization by filtration (pore size 0.2 μm), and the two major components of indigo naturalis, i.e., indigo blue (purchased from Fluka, Bucks, Switzerland) and indirubin (purchased from Alexis, Lausen, Switzerland), both being dissolved in DMSO before dilution in culture medium, were tested in the bioassays. The obtained results reveal that the anti-psoriatic effects of indigo naturalis are mediated, at least in part, by modulating the proliferation and differentiation of keratinocytes, with indirubin as the major active component (Y. K. Lin et al. (2009a), *Journal of Dermatological Science*, 54:168-174).

The applicants further investigated the anti-inflammatory effects of said indigo naturalis sample and indigo blue and indirubin, as well as tryptanthrin, in human neutrophils, and found that only said indigo naturalis sample inhibits human neutrophil proinflammatory responses, including respiratory burst and degranulation, which were mediated through blocking MAPK and $Ca^{2+}$ signaling pathways. The obtained results support the concept of developing a whole herbal extract of indigo naturalis, rather than the major component(s) contained therein, for treating neutrophilic inflammation (Y. K. Lin et al. (2009b), *Journal of Ethnopharmacology*, 125:51-58).

While organic solvents have been used to extract indigo naturalis, the products thus obtained may contain trace amounts of said organic solvents which may cause adverse effects to human body. The indigo naturalis ointment as previously developed by the applicants has the drawbacks of unpleasant odor and deep blue color that may leave stains on nails, skins and clothes, thereby affecting patients' compliance.

Therefore, the applicants developed a new formulation in which indigo naturalis powder is refined by an oil extraction, in particular by olive oil extraction, so that the major component of indigo naturalis, i.e., indigo blue, as well as impurities such as lime, is removed. This new formulation reduces the blue discoloration of nails, skins and clothes and provides less skin irritation, thus rendering psoriasis treatment more user-friendly.

SUMMARY OF THE INVENTION

Therefore, according to a first aspect, this invention provides an oil-extracted product of indigo naturalis which is obtained by a process comprising extracting indigo naturalis powder with an oil under heating, optionally followed by a refining treatment by filtration.

In a second aspect, this invention provides a process for preparing an oil-extracted product of indigo naturalis, comprising subjecting indigo naturalis powder to an extraction treatment using an oil under heating.

The oil-extracted product of indigo naturalis has been demonstrated to be effective in relieving or ameliorating human psoriatic diseases, in particular skin psoriasis and nail psoriasis. Therefore, in a third aspect, this invention provides a pharmaceutical composition comprising an oil-extracted product of indigo naturalis as described above.

In a fourth aspect, this invention provides a method for treating a human subject having or suspected to have a psoriatic disease, comprising treating said human subject with a pharmaceutical composition as described above.

BRIEF DESCRIPTION OF THE DRAWINGS

The above and other objects, features and advantages of this invention will become apparent with reference to the following detailed description and the preferred embodiments taken in conjunction with the accompanying drawings, in which.

DETAILED DESCRIPTION OF THE INVENTION

Figure 1:
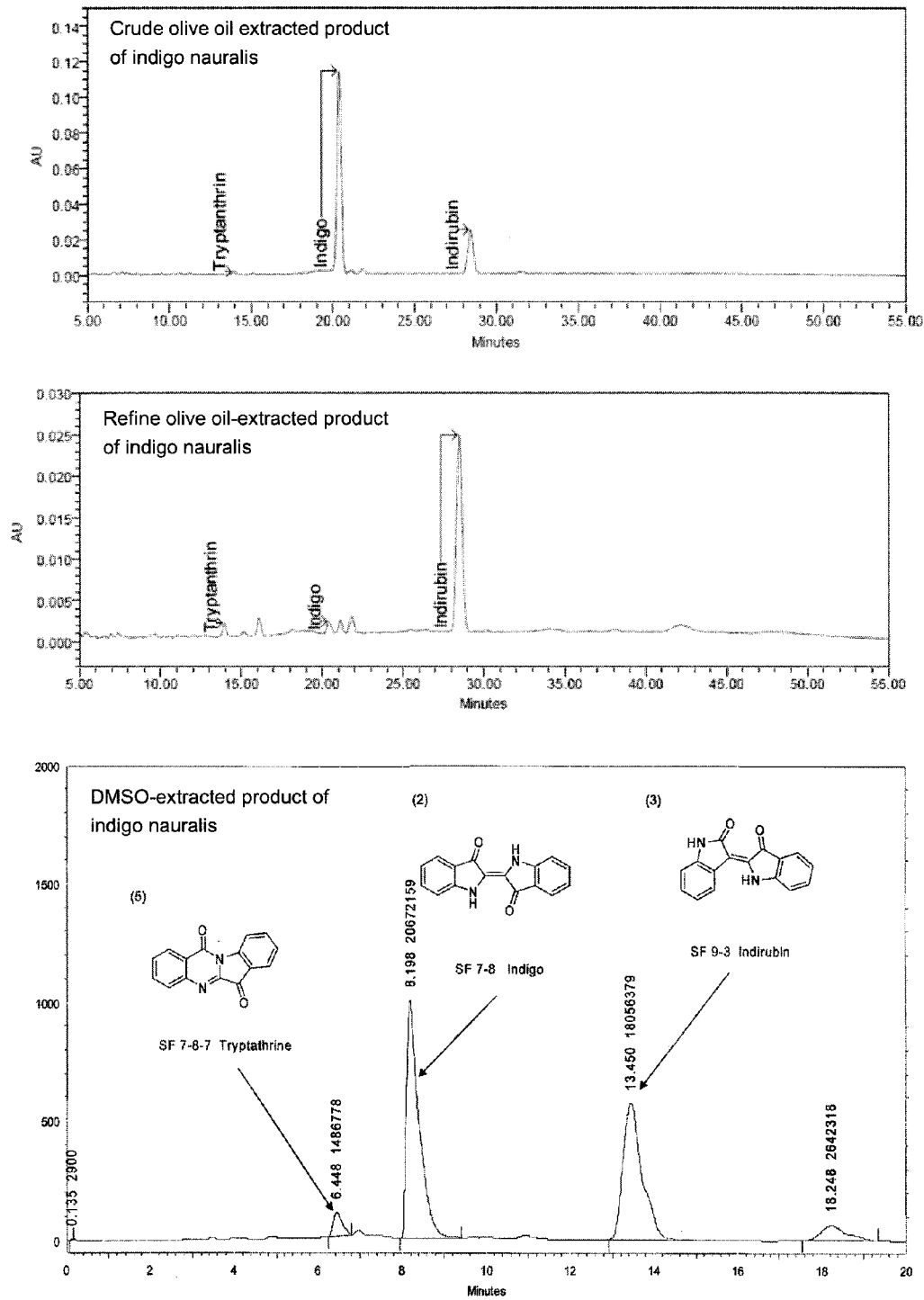
FIG. 1 shows the chromatographic fingerprints of a crude extract of indigo naturalis (upper panel) and a refined extract of indigo naturalis (middle panel) as prepared in Example 2, infra, as well as the chromatographic fingerprint of a DMSO-extracted product of indigo naturalis (lower panel) for comparison therewith.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the words "comprises," "contain" and variants thereof have a corresponding meaning.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

As used herein, the term "psoriasis" or "psoriatic disease" refers to all types of psoriasis well known to those skilled in the art. The term "psoriasis" includes, but is not limited to, chronic plaque psoriasis, guttate psoriasis, erythrodermic psoriasis, pustular psoriasis, inverse psoriasis (also known as flexural psoriasis), nail psoriasis, psoriatic arthritis, etc.

In order to develop an anti-psoriatic drug that is safe for long term use, the applicants have attempted to extract active components from indigo naturalis using different vegetable oils and various operating conditions for extraction.

Accordingly, this invention provides an oil-extracted product of indigo naturalis and a process for preparing the same. The oil-extracted product of indigo naturalis according to this invention may be obtained by extracting indigo naturalis powder with an oil under heating, optionally followed by a refining treatment by filtration.

According to the HPLC analysis results, the oil-extracted product of indigo naturalis as obtained after the oil extraction treatment was proven to contain indirubin and indigo and exhibit a blue violet color. When the refining treatment was further performed, the oil-extracted product of indigo naturalis thus obtained was found to have a decreased indigo content and exhibit a purple red color.

According to this invention, the oil suitable for use in the extraction of indigo naturalis powder is selected from the group consisting of vegetable oils, animal oils, mineral oils, and combinations thereof.

In a preferred embodiment of this invention, the oil is a vegetable oil selected from the group consisting of olive oil, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, camellia oil, grape seed oil, canola oil, castor oil, and combinations thereof. In a more preferred embodiment of this invention, the oil is a vegetable oil selected from the group consisting of olive oil, cottonseed oil, sesame oil, sunflower seed oil, peanut oil, wheat germ oil, soybean oil, and combinations thereof. In a most preferred embodiment of this invention, the oil is olive oil.

When olive oil is used, according to this invention, the oil extraction of indigo naturalis powder is preferably performed at a ratio of indigo naturalis to olive oil in a range of from 1:10 (w/v) to 1:40 (w/v). In a preferred embodiment of this invention, the ratio of 1:10 is used in the extraction of indigo naturalis powder by olive oil.

According to this invention, the oil extraction of indigo naturalis powder is preferably conducted at an elevated temperature not higher than 155° C., more preferably at a temperature ranging from 100° C. to 155° C. In a preferred embodiment of this invention, the oil extraction of indigo naturalis powder is conducted at 145° C.

According to this invention, when the process for preparing the oil-extracted product of indigo naturalis further comprises a filtration treatment to refine the product obtained from the extraction treatment, the filtration treatment may be conducted by techniques well known to and commonly used by those skilled in the art. For example, the filtration treatment may be conducted using cheese cloth, or filter paper or filter membrane which has a predetermined pore size. In a preferred embodiment of this invention, the filtration treatment is conducted using a filter paper having a pore size of 6 µm. With this filtration treatment, a refined oil-extracted product of indigo natural is obtained in which indigo and impurities such as lime will be extensively removed.

The oil-extracted products of indigo naturalis according to this invention have been proven to have potent therapeutic effects upon psoriatic lesions in human subjects, in particular psoriatic skin lesions and psoriatic nail lesions, while not causing adverse skin responses to said human subjects. Therefore, the oil-extracted products of indigo naturalis according to this invention are expected to be useful in the treatment of psoriasis. Accordingly, this invention provides a pharmaceutical composition comprising the aforesaid oil-extracted products of indigo naturalis.

This invention further provides a method for treating a human subject having or suspected to have a psoriatic disease. The method comprises treating said human subject with the pharmaceutical composition described above.

The pharmaceutical composition according to this invention can be formulated into a suitable dosage form for topical or oral administration using technology well known to those skilled in the art, which includes, but is not limited to, sterile powder, tablets, troches, pills, capsules, external preparations, suppositories, and the like.

The pharmaceutical composition according to this invention can additionally comprise a pharmaceutically acceptable carrier widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, liposomes, and the like.

Preferably, the pharmaceutical composition according to this invention is formulated into an external preparation that can be directly applied to a psoriatic lesion. The external preparation suitable for the pharmaceutical composition according to this invention may be an emulsion, a gel, an ointment, a cream, a patch, an embrocation, an aerosol, a spray, a lotion, a serum, a paste, a foam, or a drop. In a preferred embodiment of this invention, the pharmaceutical composition is formulated into an external preparation by admixing the oil-extracted product of indigo naturalis according to this invention with a base that is well known and commonly used in the art.

For example, the base suitable for producing the external preparation according to this invention may include one or more of the following additives: hydrocarbons (e.g., petroleum jelly and white petrolatum), wax (e.g., paraffin and yellow wax), preserving agents, antioxidant, surfactants, absorption enhancers, stabilizing agents, gelling agents, active agents, odor absorbers, or fragrances. The choice and amount of these additives are within the expertise of those skilled in the art.

In a preferred embodiment of this invention, the pharmaceutical composition is formulated into an ointment. In another preferred embodiment of this invention, the pharmaceutical composition is formulated into an oil drop.

The dosage and the frequency of administration of the pharmaceutical composition according to this invention may vary depending on the following factors: the severity of the disease to be treated, the route of administration, and the weight, age, physical condition and response of the subject to be treated. For instance, the daily dosage of the pharmaceutical composition according to this invention, e.g., an ointment, may be about 30 g for one application to a whole body (1 g of the ointment according to this invention may contain 0.01-1 mg of indirubin), and may be administered once daily or twice daily.

The pharmaceutical composition according to this invention may be used alone or in combination with other pharmaceutical compositions, including, but not limited to, corticosteroids, anthralin, coal tar, calcitriol, tazarotene, salicylic acid, MTX, cyclosporin, retinoids, alefacept, efalizumab, etanercept, and adalimumab.

This invention will be further described by way of the following examples. However, it should be understood that the following examples are solely intended for the purpose of illustration and should not be construed as limiting the invention in practice.

EXAMPLES

Experimental Materials

1. Indigo naturalis powder, which was prepared from the plant of *Strobilanthes formosanus* Moore (Acanthaceae) grown in the mountains near Sansia district, New Taipei City, Taiwan, was purchased from Guang Sheng Trading (Taipei, Taiwan).
2. All of the vegetable oils used in extracting indigo naturalis powder were purchased from Sigma (USA).

General Experimental Procedures:

1. Quantitative Analysis of Indirubin in Extracted Products of Indigo Naturalis by High Performance Liquid Chromatography (HPLC):

Since indirubin has been known to be one of the major active components of indigo naturalis, in the following Examples, it was used as an indicator to determine the influences of different operating conditions upon the extraction, in particular oil extraction, of indigo naturalis powder.

To determine the indirubin content thereof, an extracted product of indigo naturalis as prepared in the following Examples was subjected to a HPLC analysis using an Agilent 1100 series liquid chromatography system (Agilent Technologies, Palo Alto, Calif., USA) under the operating conditions shown in Table 1, in which indirubin (purchased from Alexis, Lausen, Switzerland; 0.1 mg/mL in chloroform) was used as a control standard.

TABLE 1

| HPLC operating conditions for quantitative analysis of indirubin. | |
| --- | --- |
| Column | Agilent ZORBAX SIL |
| Detection wavelength | UV-307 nm |
| Mobile phase | Chloroform/ethyl acetate (80:20, v/v) |
| Conditions for gradient elution | Maintaining the content of ethyl acetate at 20% during 0-12 minutes; increasing the content of ethyl acetate from 20% to 100% during 12-15 minutes; maintaining the content of ethyl acetate at 100% during 15-25 minutes; and reducing the content of ethyl acetate from 100% to 20% during 25-30 minutes. |
| Flow rate (mL/minute) | 1 |

Example 1

The Influences of Extraction Conditions Upon the Indirubin Content in Oil-Extracted Products of Indigo Naturalis A. The Influences of Different Extraction Oils Upon the Indirubin Content in Oil-Extracted Products of Indigo Naturalis In this experiment, the applicants tested seven vegetable oils, including olive oil, cottonseed oil, sesame oil, sunflower seed oil, peanut oil, wheat germ oil and soybean oil, to determine their extraction ability upon indigo naturalis powder. Briefly, 2 mL of each oil was evenly mixed with 0.1 g of indigo naturalis powder, and the resultant mixture was heated at 110° C. for 30 minutes. The seven crude oil-extracted products thus obtained, which all exhibited a blue violet color, were filtered by passing through a syringe filter (Millipore, France), respectively, and the filtrates thus collected formed the corresponding refined oil-extracted products in purple red color. For comparison, two organic solvent-extracted products were prepared by performing same extraction experiments using two different organic solvents, namely, ethyl acetate and ethanol.

100 μL of each of the extracted products of indigo naturalis as described above was 10-fold diluted with chloroform and then subjected to the HPLC analysis as set forth in the section, entitled "1. Quantitative analysis of indirubin in extracted products of indigo naturalis by high performance liquid chromatography (HPLC)," of the General Experimental Procedures, so as to determine the indirubin content thereof.

Results:

Table 2 shows the indirubin contents in extracted products of indigo naturalis as prepared from different extraction solvents. It can be seen from Table 2 that the seven refined oil-extracted products of indigo naturalis each have an indirubin content between those of the ethyl acetate- and ethanol-extracted products of indigo naturalis. In addition, amongst the seven refined oil-extracted products of indigo naturalis, the sesame oil-extracted product has the highest indirubin content, followed by the olive oil-extracted product. However, sesame oil has a complicated composition of ingredients as well as a strong smell and, according to some reports, it may induce allergy in some people. Therefore, the applicant presumed that the olive oil-extracted product of indigo naturalis might be more suitable for clinical use in terms of safety and then used this product to conduct the subsequent experiments of this invention.

TABLE 2

Indirubin contents in extracted products of indigo naturalis as prepared from different extraction solvents.

| | Extraction solvent | Indirubin content in extracted product of indigo naturalis (mg/g) |
| --- | --- | --- |
| Vegetable oil | Olive oil | 1.78 |
| | Cottonseed oil | 1.30 |
| | Sesame oil | 1.85 |
| | Sunflower seed oil | 1.36 |
| | Peanut oil | 1.56 |
| | Wheat germ oil | 1.26 |
| | Soybean oil | 1.39 |
| Organic solvent | Ethyl acetate | 2.37 |
| | Ethanol | 1.19 |

B. The Influences of Heating Temperatures Upon the Indirubin Content in Olive Oil-Extracted Products of Indigo Naturalis 1 g of indigo naturalis powder was evenly mixed with 10 mL of olive oil, and the resultant mixture was heated at a designated temperature (100° C., 110° C., 125° C., 145° C., and 155° C.) for 30 minutes, followed by passing through a syringe filter. 100 μL of the filtrate thus collected was 10-fold diluted with chloroform and then subjected to the HPLC analysis as set forth in the section, entitled "1. Quantitative analysis of indirubin in extracted products of indigo naturalis by high performance liquid chromatography (HPLC)," of the General Experimental Procedures, so as to determine the indirubin content thereof.

Results:

Table 3 shows the indirubin contents in olive oil-extracted products of indigo naturalis as prepared at different heating temperatures. It can be seen from Table 3 that indirubin can be extracted from indigo naturalis at different heating temperatures, with the highest indirubin content being obtained at 145° C. The applicants then used 145° C. as the heating temperature in the subsequent experiments.

TABLE 3

Indirubin contents in olive oil-extracted products of indigo naturalis as prepared at different heating temperatures.

| Heating temperature (° C.) | Indirubin content in olive oil-extracted product of indigo naturalis (mg/g) |
|---|---|
| 100 | 3.22 |
| 110 | 3.42 |
| 125 | 4.18 |
| 145 | 4.66 |
| 155 | 4.3 |

C. Selection of the Ratio of Indigo Naturalis Powder to Olive Oil

Indigo naturalis powder at a designated amount (1 g, 0.5 g, and 0.25 g) was evenly mixed with 10 mL of olive oil so as to provide a mixture having a ratio of indigo naturalis to olive oil at 1:10, 1:20 or 1:40 (w/v). The mixture was heated at 100° C. for 30 minutes, followed by passing through a syringe filter. 100 μL of the filtrate thus collected was 10-fold diluted with chloroform and then subjected to the HPLC analysis as set forth in the section, entitled "1. Quantitative analysis of indirubin in extracted products of indigo naturalis by high performance liquid chromatography (HPLC)," of the General Experimental Procedures, so as to determine the indirubin content thereof.

Results:

The indirubin contents in olive oil-extracted products of indigo naturalis as prepared at different ratios of indigo naturalis to olive oil (1:10, 1:20 and 1:40, w/v) are shown in Table 4. The applicants found that no significant difference was present amongst the indirubin contents of the three olive oil-extracted products of indigo naturalis thus obtained. Further, under a fixed amount of indigo naturalis powder, an increase of the used amount of olive oil failed to significantly increase the indirubin content in the olive oil-extracted product of indigo naturalis, but rather would result in a dilution of the active components contained in the extracted product. Thus, to economically obtain an olive oil-extracted product of indigo naturalis that has a saturated concentration of indirubin, the applicants decided to select the ratio of 1:10 in the extraction of indigo naturalis powder by olive oil.

TABLE 4

Indirubin contents in olive oil-extracted products of indigo naturalis as prepared at different ratios of indigo naturalis to olive oil.

| Ratio of indigo naturalis to olive oil (w/v) | Indirubin content in olive oil-extracted product of indigo naturalis (mg/g) |
|---|---|
| 1:10 | 3.2 |
| 1:20 | 3.44 |
| 1:40 | 3.48 |

Based on the experimental results obtained in the preceding sections A-C, the preferred oil extraction conditions for indigo naturalis were determined and are outlined in Table 5.

TABLE 5

Preferred operating conditions for oil extraction of indigo naturalis.

| | |
|---|---|
| Oil solvent | Olive oil |
| Heating temperature | 145° C. |
| Extraction time | 30 minutes |
| Ratio of indigo naturalis to olive oil (w/v) | 1:10 |

Example 2

Large-Scale Preparation of Olive Oil-Extracted Product of Indigo Naturalis According to this Invention Following the operating conditions shown in Table 5, 90 g of indigo naturalis powder was mixed with 900 mL of olive oil in a stainless steel pot, followed by heating at 145° C. for 30 minutes, such that a crude extract of indigo naturalis in blue violet color was obtained. The same extraction treatment of indigo naturalis powder was repeated to provide a second crude extract of indigo naturalis, which was further filtered through a filter paper having a pore size of 6 μm, thereby providing a refined extract of indigo naturalis in purple red color. The crude and refined extracts of indigo naturalis thus obtained were used in the following experiments.

To verify the major component distribution thereof, both of the crude and refined extracts of indigo naturalis as prepared above were subjected to the HPLC analysis as set forth in the section, entitled "1. Quantitative analysis of indirubin in extracted products of indigo naturalis by high performance liquid chromatography (HPLC)," of the General Experimental Procedures. For comparison, a DMSO-extracted product of indigo naturalis, which was prepared as previously described (Y. K. Lin et al. (2009a) and Y. K. Lin et al. (2009b), supra), was also analyzed.

Referring to FIG. 1, it can be seen that both of the crude (upper panel) and refined (middle panel) extracts of indigo naturalis have a chromatographic fingerprint different from that of the DMSO-extracted product of indigo naturalis (lower panel). Besides, as compared to the crude extract of indigo naturalis, the indigo content in the refined extract of indigo naturalis was significantly reduced.

Example 3

Therapeutic Effect, Safety and Convenience Evaluations of Indigo Naturalis Ointments Formulated According to this Invention in Treating Human Skin Psoriasis In order to examine the therapeutic effect, safety and convenience of the crude and refined extracts of indigo naturalis as prepared in the above Example 2 in treating human skin psoriasis, the following tests were conducted.

A. Preparation of Crude and Refined Indigo Naturalis Ointments 900 mL of each of the crude and refined extracts of indigo naturalis as prepared in the above Example 2 was admixed with 90 g of yellow wax and 90 g of petroleum jelly, so that a crude ointment containing the crude extract of indigo naturalis and a refined ointment containing the refined extract of indigo naturalis were obtained, respectively.

B. Screening of Test Subjects and Clinical Information Thereof.

Test subjects participating in the following pre-clinical tests were enrolled from the Chinese medicine outpatient department of Chang Gung Memorial Hospital, Taiwan. These test subjects were required to meet all of the inclusion and exclusion criteria as outlined in Table 6. The tests were approved by the Institutional Review Board of Chang Gung Memorial Hospital, and written informed consent was obtained from each of the test subjects.

TABLE 6

Inclusion and exclusion criteria used to screen test subjects.

| Inclusion criteria | 1 | The subject was diagnosed with plaque psoriasis by a dermatologist. |
|---|---|---|
| | 2 | The subject had a total psoriatic lesion area no more than 60% of the total skin surface area of the body. |
| | 3 | The subject had at least two lesions with similar degrees of severity on the body thereof. |
| | 4 | The subject was in good health condition and had no abnormality in liver and kidney function as well as hematology. |
| | 5 | The subject was a male or a female aged between 20 and 75 years. |
| | 6 | If the subject was a female of childbearing age, she agreed to use contraception during the test. |
| Exclusion criteria | 1 | The subject had a history of allergy to at least one of the components of the test pharmaceutical composition. |
| | 2 | The subject had received a phototherapy or a therapy using a systemic anti-psoriasis drug (such as retinoids, cyclosporin, MTX, etc.) within 4 weeks before the test. |
| | 3 | The subject had received a therapy using a local anti-psoriasis drug (such as coal tar, corticosteroids, vitamin $D_3$ analogues, etc.) within 2 weeks before the experiment. |
| | 4 | The subject had a medical history of non-plaque (i.e., pustular or erythrodermic) psoriasis or drug-induced psoriasis. |
| | 5 | The subject had mental illness, diabetes, liver or kidney disease, cancer, or AIDS. |
| | 6 | The female subject had to perform breastfeeding, was pregnant, or was preparing for pregnancy. |
| | 7 | The subject was unavailable for evaluation at designated time points during the test. |

A total of 38 test subjects participated in the following pre-clinical test, and the clinical information thereof, including gender, age, duration of psoriasis, psoriasis area and severity index (PASI) and the percentage of body surface area involved in psoriasis, are outlined in Table 7.

TABLE 7

Clinical information of 38 test subjects enrolled in the pre-clinical test.

| | | Mean ± SD | Range |
|---|---|---|---|
| Gender | Male (total) | 31 | — |
| | Female (total) | 7 | — |
| Age (year) | | 42.8 ± 12.7 | 23~63 |
| Duration of psoriasis (year) | | 12.2 ± 10.5 | 1~45 |

TABLE 7-continued

Clinical information of 38 test subjects enrolled in the pre-clinical test.

| | Mean ± SD | Range |
|---|---|---|
| PASI | 11.5 ± 7.8 | 1.6~36.1 |
| The percentage of body surface area involved in psoriasis (%) | 19.0 ± 14.7 | 2~60 |

C. Pre-Clinical Test

Prior to the start of the test (i.e., on Week 0), two lesions with similar degree of severity were selected from the body (excluding the head and the neck) of each of the 38 test subjects enrolled and then separately photographed and subjected to measurement of the lesion area, with the obtained data being expressed as $cm^2$.

The crude and refined ointments of indigo naturalis as prepared in the preceding section A were applied to the two selected lesions of each test subject once daily at a dose of 1 g/100 $cm^2$ of the lesion area for a period of eight weeks, respectively. At the ends of Weeks 2, 4, 6, and 8, the treated lesions were separately photographed and subjected to measurement of the lesion area. To determine the therapeutic effect, safety and convenience of the two tested ointments, the treated lesions were evaluated according to the methods set forth in sections D and E below.

During the test time, three male test subjects failed to complete the ointment treatment, in which the first one withdrew from the test at Week 4 due to work, the second one withdrew due to the development of an itchy condition at the treated areas at Week 5, and the third one withdrew at Week 6 due to moving house. Thus, only 35 test subjects successfully completed the pre-clinical test.

D. Evaluation of Therapeutic Effect

Figure 2:
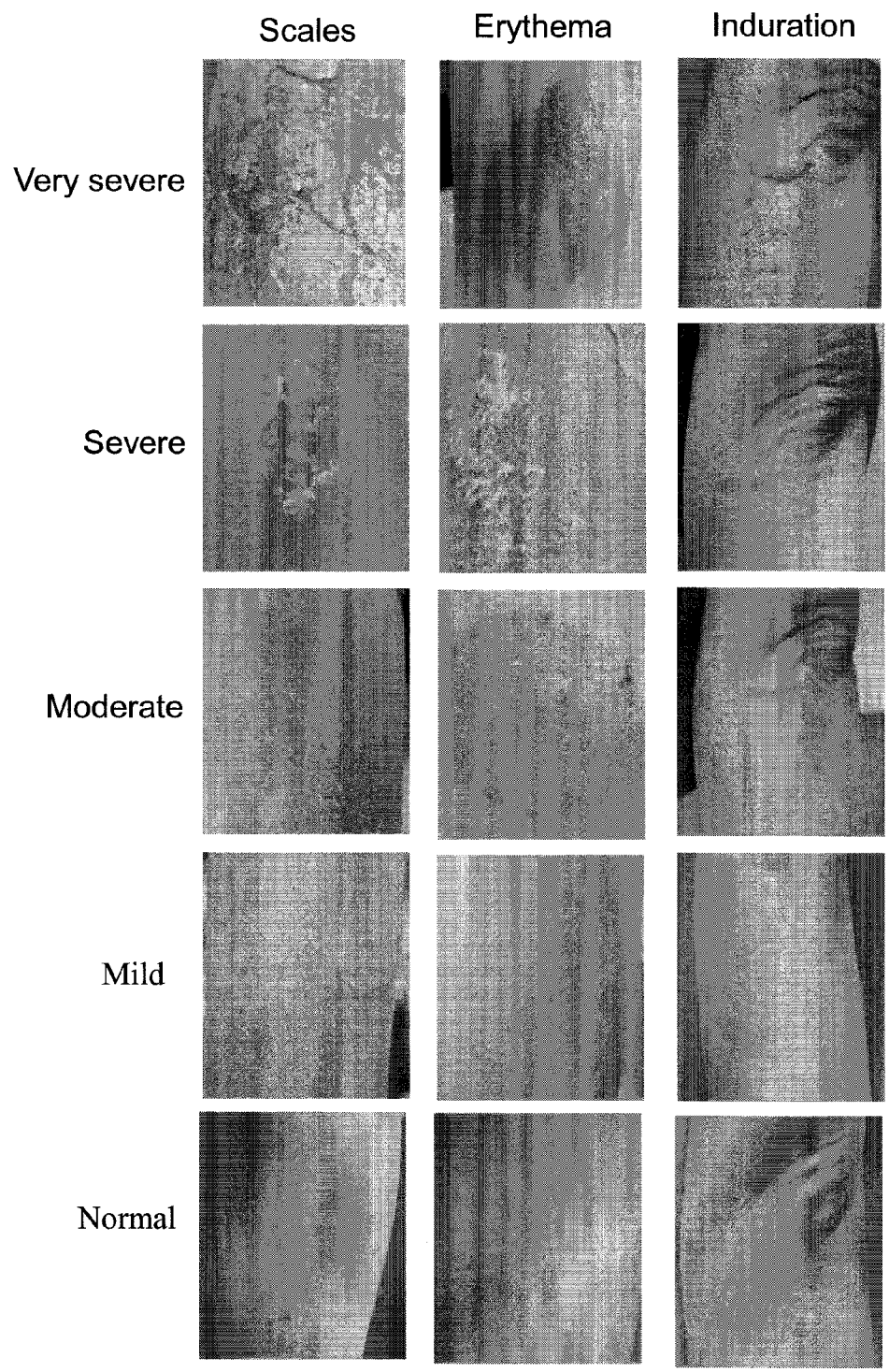
FIG. 2 shows the standard reference photos used to rate the degrees of severity of psoriasis based on scales, erythema and induration.

1. Evaluation of the Degrees of Severity of Psoriasis Based on Scales, Erythema and Induration:

The photos of the selected lesions of the test subjects as obtained at Week 0 (i.e., prior to the application of the test ointments of indigo naturalis) and at the ends of Weeks 2, 4, 6, and 8 after starting the application of the test ointments of indigo naturalis were compared with the standard reference photos as shown in FIG. 2 by a dermatologist. Based on said standard reference photos, the degrees of scales, erythema and induration were ranked with a score ranging from 0 to 4, respectively, in which 0=normal, 1=mild, 2=moderate, 3=severe, and 4=very severe. The therapeutic effect of a test ointment was then determined based on the scores of scales, erythema and induration respectively calculated at the designated time points (Week 0, 2, 4, 6 and 8), as well as the sums of said three scores calculated.

The experimental data thus obtained for all of the selected lesions of the test subjects were expressed as mean±SD and plotted versus time. Paired t-test or Wilcoxon signed rank test was used to compare the scores of scales, erythema and induration between the two lesions, where appropriate. Paired t-test was also conducted to compare the scores of scales, erythema and induration between the pre- and post-treatments. The mixed-effect model was used to account for time dependency of the repeated measurement and differences between the two lesions. Statistical significance was indicated by $p<0.05$.

2. Evaluation of the Change in Lesion Area:

The lesion areas of the selected lesions of the test subjects as measured at Week 0 (i.e., prior to the application of the test ointments of indigo naturalis) and at the ends of Weeks 2, 4, 6, and 8 after starting the application of the test ointments of indigo naturalis were introduced into the following equation (1) to determine the changes in lesion areas with time caused by the test ointments.

$$C=(B/A)\times 100 \quad (1)$$

wherein:
A=the value of a lesion area (expressed as cm$^2$) measured at Week 0 (i.e., the baseline value).
B=the value of the lesion area (expressed as cm$^2$) measured at a designated time point (Week 0, 2, 4, 6 and 8); and
C=the percentage value of the lesion area relative to the baseline value at the designated time point.

The experimental data thus obtained for all of the selected lesions of the test subjects were expressed as mean±SD and plotted versus time and statistically analyzed as described above.

3. Evaluation of the Improvement of the Outer Appearance of Psoriatic Lesion:

To determine the improving effect of each test ointment of indigo naturalis upon the outer appearance of psoriatic lesion, the value of the sum of the scores of scales, erythema and induration as calculated for a selected lesion at a designated time point (Week 0, 2, 4, 6 and 8) in the preceding Sub-section 1 was multiplied with the corresponding percentage value of the lesion area relative to the baseline value at the designated time point as obtained in the preceding Sub-section 2, such that an "area and severity score" for said selected lesion at the designated time point was obtained. The area and severity scores thus calculated for all of the selected lesions of the test subjects were subsequently introduced into the following equation (2):

$$F=[(D-E)/D]\times 100 \quad (2)$$

wherein:
D=the area and severity score calculated for a selected lesion at Week 0 (i.e., the baseline value);
E=the area and severity score calculated for the selected lesion at a designated time point (Week 2, 4, 6 and 8); and
F=the percentage improvement of the selected lesion relative to the baseline at the designated time point.

The experimental data thus obtained for all of the selected lesions of the test subjects were expressed as mean±SD and plotted versus time and statistically analyzed as described above.

4. Overall Evaluation of the Improvement of the Psoriatic Lesion:

To evaluate the overall improvement provided by each test ointment of indigo naturalis, the photos of the selected lesions as obtained at the end of Week 8 for the 35 test subjects that completed the pre-clinical test were visually compared by a dermatologist with the corresponding photos obtained at Week 0. The extent of improvement, i.e., the observed change of the lesion shown in the photo obtained at the end of Week 8 as compared to that shown in the corresponding photo obtained at Week 0, was ranked with a score ranging from 0 to 5, in which 0=worse, 1=no change, 2=slightly improved, 3=moderately improved, 4=nearly disappeared, and 5=disappeared. Meanwhile, each of the test subjects was instructed to provide a self-overall evaluation by visually observing the selected lesions and ranking the same based on the above scoring method.

According to the dermatologist's overall evaluation and the test subjects' self-overall evaluations, the numbers of test subjects having the same ranking scores were counted, respectively, followed by calculating the percentages of said numbers of test subjects relative to the total number of test subjects. The data thus obtained were analyzed using the McNemar test so as to determine the correlation between the experimental results of the crude ointment group and those of the refined ointment group.

E. Evaluation of Safety and Convenience

Evaluation of safety was conducted by a researcher at the ends of Weeks 2, 4, 6, and 8 after starting the application of the test ointments of indigo naturalis. The test subjects were interrogated by the researcher in respect to the appearance of any adverse skin response (including itching, irritation and erythema), and the results were recorded according to the following ranking scores: 0=nil, 1=mild, 2=moderate, and 3=severe. The convenience of the crude and refined ointments of indigo naturalis was evaluated according to the response of each of the test subjects at the end of the pre-clinical test.

Figure 3:
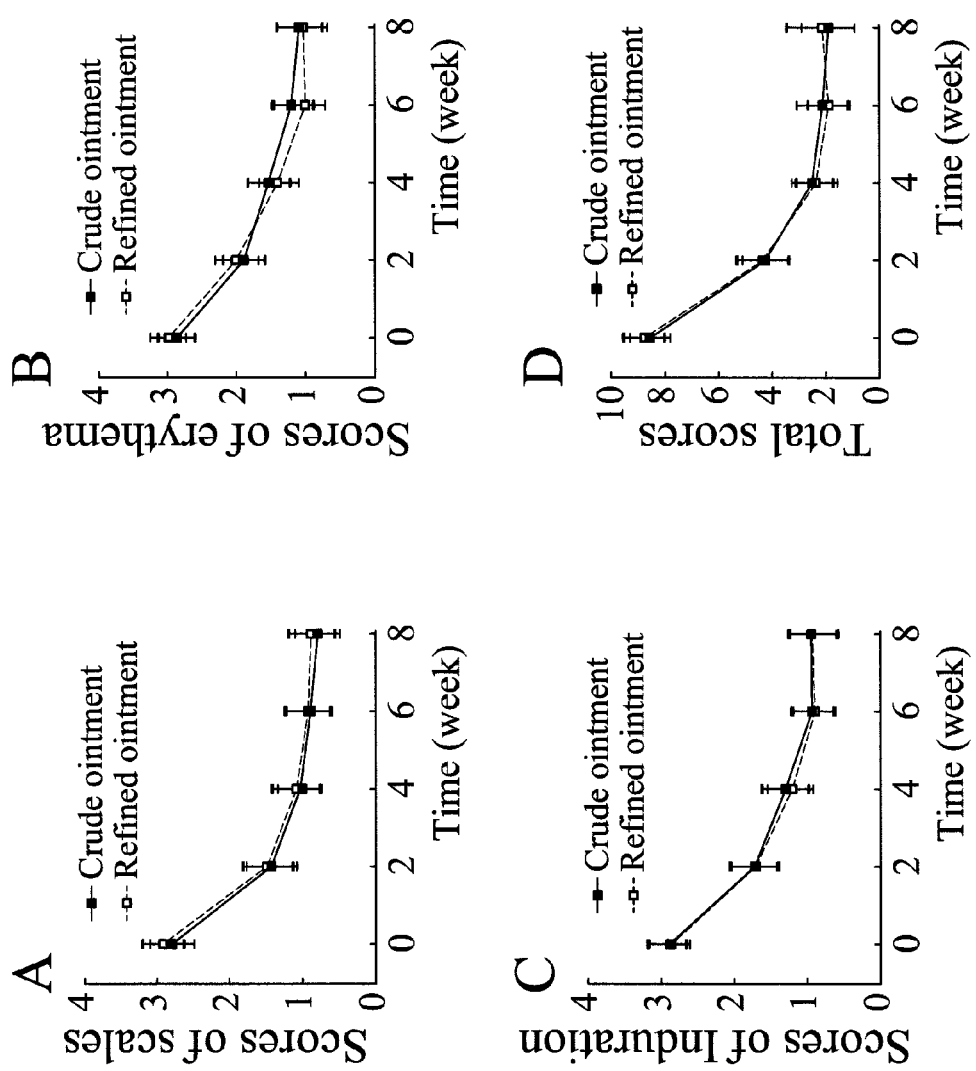
FIG. 3 shows the therapeutic effects of a crude ointment of indigo naturalis (formulated with a crude olive oil-extracted product as prepared in Example 2, infra) and a refined ointment of indigo naturalis (formulated with a refined olive oil-extracted product as prepared in Example 2, infra) in treating psoriatic lesions for a period of 8 weeks, in which panels A, B and C show the scores of scales, erythema and induration as calculated at different time points (Week 0, 2, 4, 6 and 8), respectively, and panel D shows the sums of these three scores as calculated at different time points (Week 0, 2, 4, 6 and 8); and all of the calculated scores are expressed as mean±SD.

Results:

A. Evaluation of the Therapeutic Effects of the Crude and Refined Ointments of Indigo Naturalis FIG. 3 shows the therapeutic effects of the crude and refined ointments of indigo naturalis as prepared in the above Example 2. It can be seen from the results shown in panels A, B, C and D of FIG. 3 that the scores of scales, erythema and induration were significantly lowered with time due to the ointment treatment, respectively, as compared to the corresponding scores calculated at Week 0. Besides, no significant difference was found to exist between the crude ointment group and the refined ointment group at the same time point.

Figure 4:
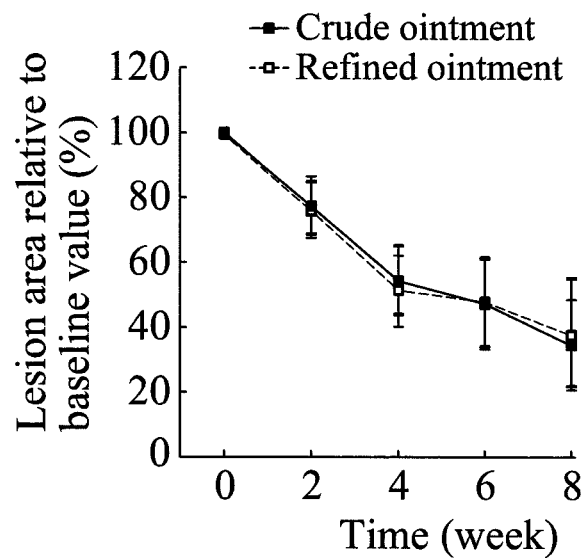
FIG. 4 is a plot showing the changes in lesion areas with time caused by the crude and refined ointments of indigo naturalis as prepared in Example 2, infra, in which the average percentage values of the lesion areas relative to the baseline value as calculated at different time points (Week 0, 2, 4, 6 and 8) were plotted, and the data were expressed as mean±SD.
Figure 5:
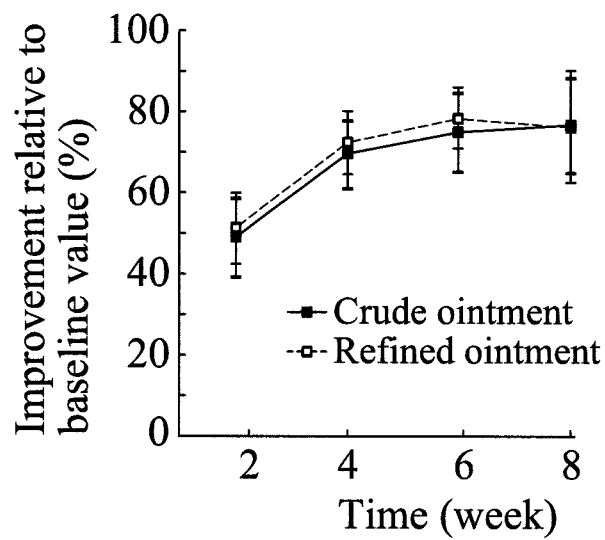
FIG. 5 is a plot showing the improvement of the outer appearance of psoriatic lesions treated with the crude and refined ointments of indigo naturalis as prepared in Example 2, infra, in which the percentage improvements of the treated lesions relative to the baseline as calculated at different time points (Week 0, 2, 4, 6 and 8) were plotted, and the data were expressed as mean±SD.

FIG. 4 shows the changes in lesion areas with time caused by the crude and refined ointments of indigo naturalis as prepared in the above Example 2, and FIG. 5 shows the improvement of the outer appearance of psoriatic lesions treated with the crude and refined ointments of indigo naturalis as prepared in the above Example 2. It can be seen from FIG. 4 and FIG. 5 that the average percentage values of the lesion areas relative to the baseline value were significantly lowered with time due to the ointment treatment, while the percentage improvements of the treated lesions relative to the baseline were significantly increased with time due to the ointment treatment, as compared to the corresponding data obtained at Week 0. Besides, no significant difference was found to exist between the crude ointment group and the refined ointment group at the same time point.

The above experimental results reveal that both of the crude and refined ointments of indigo naturalis according to this invention are effective in relieving psoriatic lesions and they have no significant difference in therapeutic efficacy.

The overall improvements of psoriatic lesions as provided by the test ointments of indigo naturalis were further evaluated by a dermatologist and the 35 test subjects that completed the pre-clinical test at the end of the test, and the obtained results are summarized in Table 8.

TABLE 8

The overall improvements of psoriatic lesions as evaluated by a dermatologist and the test subjects.

| | Evaluation by test subjects | | Evaluation by dermatologist | |
|---|---|---|---|---|
| | Refined ointment | Crude ointment | Refined ointment | Crude ointment |
| Disappeared (5[a]) | 12[b] (34.3%[c]) | 8 (22.9%) | 19 (54.3%) | 18 (51.4%) |
| Nearly disappeared (4) | 11 (31.4%) | 13 (37.1%) | 3 (8.6%) | 3 (8.6%) |
| Moderately improved (3) | 9 (25.7%) | 11 (31.4%) | 6 (17.1%) | 6 (17.1%) |

TABLE 8-continued

The overall improvements of psoriatic lesions as evaluated by a dermatologist and the test subjects.

| | Evaluation by test subjects | | Evaluation by dermatologist | |
|---|---|---|---|---|
| | Refined ointment | Crude ointment | Refined ointment | Crude ointment |
| Slightly improved (2) | 1 (2.9%) | 1 (2.9%) | 3 (8.6%) | 3 (8.6%) |
| No change (1) | 1 (2.9%) | 1 (2.9%) | 1 (2.9%) | 2 (5.7%) |
| Worse (0) | 1 (2.9%) | 1 (2.9%) | 3 (8.6%) | 3 (8.6%) |
| Correlation | 0.70 | | 0.83 | |

[a]A ranking score as indicated.
[b]The number of test subjects having a ranking score as indicated.
[c]The percentage of said number of test subjects relative to the total number of test subjects.

It can be seen from Table 8 that not only the dermatologist but also most of the test subjects considered the crude and refined ointments of indigo naturalis according to this invention to be effective in relieving psoriatic lesions and to exhibit similar therapeutic effects.

B. Evaluation of the Safety and Convenience of the Crude and Refined Ointments of Indigo Naturalis Table 9 shows the safety evaluation results of the crude and refined ointments of indigo naturalis as prepared in the above Example 2. It can be seen from Table 9 that amongst the test subjects that completed the test, only a few of them experienced temporary and mild adverse skin responses, including itching, irritation and erythema, which, however, did not halt them from completing the test. Particularly, the crude ointment of indigo naturalis was found to have a higher score as compared to the refined ointment of indigo naturalis, indicating that the crude olive-oil extract of indigo naturalis could be refined by filtration to remove any possible impurities and undesired pigment contained therein, thereby reducing the incidence of adverse skin response(s).

TABLE 9

Safety evaluation results of the crude and refined ointments of indigo naturalis.

| | | Adverse skin response | | | Total score |
|---|---|---|---|---|---|
| | | Itching | Irritation | Erythema | |
| Crude ointment | Week 2 | 1[a] × 6[b], 2 × 1 | — | 1 × 1, 2 × 1 | 32 |
| | Week 4 | 1 × 5 | 1 × 1 | 1 × 2 | |
| | Week 6 | 1 × 4 | 1 × 1 | 1 × 2 | |
| | Week 8 | 1 × 5 | — | 1 × 1 | |
| Refined ointment | Week 2 | 1 × 5 | 1 × 1 | — | 17 |
| | Week 4 | 1 × 1 | 1 × 2 | — | |
| | Week 6 | 1 × 4 | 1 × 2 | 1 × 1 | |
| | Week 8 | 1 × 1 | — | — | |

[a]An indicated ranking score for evaluating the degree of an adverse skin response.
[b]The number of test subjects having the ranking score as indicated.

At the end of the pre-clinical test, the conveniences of the crude and refined ointments of indigo naturalis were evaluated according to the responses of the 35 test subjects that completed the test, amongst which 31 test subjects (88.6%) reported that the refined ointment of indigo naturalis was more user-friendly than the crude ointment of indigo naturalis, 3 test subjects (8.6%) reported that there was no difference between the crude and refined ointments of indigo naturalis, and only 1 test subject (2.9%) reported that the crude ointment of indigo naturalis was better than the refined ointment of indigo naturalis. The applicants then concluded that the refined olive oil-extracted product of indigo naturalis, which was obtained by subjecting the crude olive oil-extracted product of indigo naturalis to a refining treatment by filtration and, hence, had relatively less impurities and a relatively light color, would be less likely to induce adverse skin reaction(s) or cause a discoloration of skins or clothes, thereby making the refined ointment of indigo naturalis more user-friendly and increasing patient compliance in using the same.

Example 4

Therapeutic Effect and Safety Evaluations of Indigo Naturalis Oil Drop in Treating Human Nail Psoriasis In order to examine the therapeutic effect and safety of the refined extract of indigo naturalis as prepared in the above Example 2 in treating human nail psoriasis, the following tests were conducted.

A. Preparation of Indigo Naturalis Oil Drop and Olive Oil Drop

The refined extract of indigo naturalis as prepared in the above Example 2 was dispensed into dropper bottles to serve as the indigo naturalis oil drop tested below. In the meantime, olive oil was dispensed into dropper bottles to serve as the olive oil drop tested below.

B. Screening of Test Subjects and Clinical Information Thereof

Test subjects participating in the following pre-clinical tests were enrolled from the Chinese medicine outpatient department of Chang Gung Memorial Hospital, Taiwan. These test subjects were required to meet all of the inclusion and exclusion criteria outlined in Table 10. The tests were approved by the Institutional Review Board of Chang Gung Memorial Hospital, and written informed consent was obtained from each of the test subjects.

TABLE 10

Inclusion and exclusion criteria used to screen test subjects.

| Inclusion criteria | 1 | The subject was diagnosed by a dermatologist to have nail psoriasis, singly or in combination with skin psoriasis. |
|---|---|---|
| | 2 | The subject was in good health condition and had no abnormality in liver and kidney function as well as hematology. |
| | 3 | The subject was a male or a female aged between 20 and 65 years. |
| | 4 | If the subject was a female of childbearing age, she agreed to use contraception during the test. |
| Exclusion criteria | 1 | The subject had a history of allergy to indigo naturalis. |
| | 2 | The subject had received a therapy using an anti-psoriasis drug such as retinoids, cyclosporin, MTX, etc., or a biologics injection therapy. |
| | 3 | The female subject had to perform breastfeeding, was pregnant, or was preparing for pregnancy. |
| | 4 | The subject was unavailable for evaluation at designated time points during the test. |

A total of 31 test subjects participated in the following pre-clinical test, and the clinical information thereof, including gender, age, duration of psoriasis, PASI, etc., are outlined in Table 11.

TABLE 11

Clinical information of 31 test subjects enrolled in the pre-clinical test.

|  |  | Mean ± SD | Range |
|---|---|---|---|
| Gender | Male (total) | 24 | — |
|  | Female (total) | 7 | — |
| Age (year) |  | 40.7 ± 12.6 | 21~65 |
| Duration of skin psoriasis (year) |  | 9.4 ± 6.6 | 0~22 |
| Duration of nail psoriasis (year) |  | 5.2 ± 5.5 | 0.5~21 |
| Family history of psoriasis |  | 7 | — |
| Psoriatic arthritis |  | 8 | — |
| PASI |  | 9.0 ± 8.6 | 0~42.6 |
| The percentage of body surface area involved in psoriasis (%) |  | 15.3 ± 19.9 | 0~99 |
| Number of fingers having nail psoriasis |  | 9.4 ± 1.1 | 5~10 |

C. Pre-Clinical Test

The left and right hands of each of the test subjects were randomly divided into the experimental group and the control group, and the psoriatic nail lesions were photographed. The test subjects were instructed to apply the indigo naturalis oil drop onto the nail plate, nail fold and hyponychium of the affected fingernails at a dose of 0.05~0.1 mL per fingernail twice daily (at morning and bedtime), and they were also instructed not to wash hands within at least 30 minutes after application, as well as avoiding any activity that might cause injury to the fingernails. The test time for the experimental group lasted for a period of 24 weeks in toto.

In the meantime, the fingernails in the control group were applied with the olive oil drop in the same way as described above for the experimental group for a period of 12 weeks, and then applied with the indigo naturalis oil drop for a further period of 12 weeks.

At the ends of Weeks 4, 8, 12, 16, 20 and 24 during the test time, the fingernails in the experimental group and those in the control group of each test subject were separately photographed and then evaluated according to the methods set forth in sections D and E below.

During the test time, 4 test subjects withdrew from the test at Week 8, 16, 20 and 24, respectively, for failure to apply the oil drop as instructed. Thus, only 27 test subjects successfully completed the pre-clinical test.

D. Evaluation of Therapeutic Effect

1. Evaluation of Nail Psoriasis by Nail Psoriasis Severity Index (NAPSI):

The photos of the fingernails in the experimental group and those in the control group as obtained at Week 0 (i.e., prior to the application of the test oil drop) and at the ends of Weeks 4, 8, 12, 16, 20, and 24 after starting the application of the test oil drop were subjected to a NAPSI evaluation according the rules established in Table 1 of P. Rich and R. K. Scher (2003), *J. Am. Acad. Dermatol.*, 49(2):206-212, in which the clinical features used in the NAPSI evaluation are outlined in Table 12, so as to calculate the total NAPSI scores, as well as the individual NAPSI scores of said clinical features, of the fingernails in the experimental group and those in the control group at the designated time points (Weeks 0, 4, 8, 12, 16, 20, and 24). The individual NAPSI scores as calculated based on the photos of fingernails obtained at the end of Week 12 were compared with those calculated based on the photos of fingernails obtained at Week 0, so as to determine the improving effect(s) of the indigo naturalis oil drop upon the clinical features of the fingernails of the test subjects.

The experimental data thus obtained were expressed as mean±SD, and were statistically analyzed using a mixed effect model, followed by the Bonferroni test, so as to determine the difference(s) between different time points for a test group, and the difference(s) between the experimental group and the control group at the same time point. Statistical significance was indicated by $p<0.05$.

TABLE 12

Clinical features used in the NAPSI evaluation of nail psoriasis.

| | Clinical features |
|---|---|
| Nail matrix psoriasis | Pitting |
|  | Leukonychia |
|  | Red spots in the lunula |
|  | Nail plate crumbling |
| Nail bed psoriasis | Onycholysis |
|  | Splinter hemorrhages |
|  | Subungual hyperkeratosis |
|  | Nail bed discoloration |

2. Evaluation of Nail Psoriasis by a Modified Target NAPSI:

For every test subject, a target fingernail that was considered to have the highest disease severity was respectively selected from the five fingers shown in the photos of the experimental group and the control group obtained at Week 0, and said target fingernail was then subjected to a modified target NAPSI evaluation according to the rules reported in C. A. Parrish et al. (2005), *J. Am. Acad. Dermatol.*, 53 (4):745-746, using the clinical features outlined in Table 12, so as to calculate the total modified target NAPSI score of said target fingernail at the designated time points (Weeks 0, 4, 8, 12, 16, 20, and 24).

The experimental data thus obtained were expressed as mean±SD, and were statistically analyzed as described above for the NAPSI evaluation.

3. Evaluation of the Improvement of the Nail Psoriasis:

To determine the improving effect of the indigo naturalis oil drop upon nail psoriasis, the total NAPSI scores or the total modified target NAPSI scores calculated for each test subject was introduced into the following equation (3):

$$J=[(G-H)/G]\times 100 \quad (3)$$

wherein:
G=the total NAPSI score or the total modified target NAPSI score calculated for a test group at Week 0 (i.e., the baseline value);
H=the total NAPSI score or the total modified target NAPSI score calculated for the test group at a designated time point (Week 12 and 24); and
J=the percentage improvement of nail psoriasis relative to the baseline at the designated time point.

The experimental data thus obtained were expressed as mean±SD, and were statistically analyzed as described above for the NAPSI evaluation.

4. Overall Evaluation of the Improvement of the Nail Psoriasis:

To evaluate the overall improvement provided by the indigo naturalis oil drop, the photos of fingernails as obtained at the ends of Weeks 12 and 24 for the test subjects were visually compared by a dermatologist with the corresponding photos obtained at Week 0, in which the extent of improvement, i.e., the observed change of fingernails shown in the photo obtained at the end of Weeks 12 or 24 as compared to that shown in the corresponding photo obtained at Week 0, was ranked with a score ranging from 0 to 5, in which 0=worse, 1=no change, 2=slightly improved, 3=moderately improved, 4=nearly disappeared, and 5=disappeared. Meanwhile, each of the test subjects was instructed to provide a self-overall evaluation by visually observing their own fingernails and ranking the same based on the above scoring method.

According to the dermatologist's overall evaluation and the test subjects' self-overall evaluations, the numbers of test subjects having the same ranking scores were counted, respectively, followed by calculating the percentages of said numbers of test subjects relative to the total number of test subjects.

E. Evaluation of Safety

Evaluation of safety was conducted by a researcher at the ends of Weeks 4, 8, 12, 16, 20 and 24 after starting the application of the indigo naturalis oil drop. The test subjects were interrogated by the researcher in respect to the appearance of any adverse skin response (including itching, irritation and erythema), and the results were recorded according to the following ranking scores: 0=nil, 1=mild, 2=moderate, and 3=severe. Results:

A. Evaluation of the Therapeutic Effect of the Indigo Naturalis Oil Drop

Table 13 shows the changes of the total NAPSI scores, the total modified target NAPSI scores and the percentage improvements of nail psoriasis of the fingernails in the experimental and control groups with time. It can be seen from Table 13 that during the first period of 12 weeks, application of the indigo naturalis oil drop resulted in a lowering of the total NAPSI scores and the total modified target NAPSI scores of the fingernails with time, and a significant improvement of nail psoriasis was found in the experimental group as compared to the control group at the end of Week 12. During the second period of 12 weeks, the total NAPSI scores and the total modified target NAPSI scores were lowered with time in both of the experimental and control groups. In addition, a significant improvement of nail psoriasis was found in both of the experimental and control groups at the end of Week 24.

For the 30 test subjects that completed the preclinical test during the first period of 12 weeks, their fingernails were subjected to the NAPSI evaluation based on the clinical features of nail psoriasis as outlined in Table 12, and the experimental results thus obtained are summarized in Table 14.

It can be seen from Table 14 that pitting has the highest incidence amongst the four clinical features of nail matrix psoriasis, followed by nail plate crumbling, while onycholysis has the highest incidence amongst the four clinical features of nail bed psoriasis, followed by nail bed discoloration and subungual hyperkeratosis. In addition, the clinical feature of red spots in the lunula was not observed for any test subject.

In general, the individual NAPSI scores of the fingernails in the experimental group as calculated at the end of Week 12 were lower than those calculated at the end of Week 0. In addition, as compared to the control group, the clinical features of nail psoriasis, in particular nail bed discoloration, onycholysis and pitting, of the fingernails in the experimental group were significantly improved at the end of Week 12. The experimental results shown in Table 14 reveal that the indigo naturalis oil drop is effective in improving the clinical fea-

TABLE 13

The therapeutic effect evaluation of the indigo naturalis oil drop by the NAPSI scoring and the modified target NAPSI scoring.

|  |  |  | NAPSI scoring | | Modified target NAPSI scoring | |
| --- | --- | --- | --- | --- | --- | --- |
| Group | Detecting time | Number of test subjects | Total NAPSI score (mean ± SD) | Percentage improvement of nail psoriasis | Modified target NAPSI score (mean ± SD) | Percentage improvement of nail psoriasis |
| EXP. | Week 0 | 31 | 21.3 ± 8.2 | — | 13.5 ± 5.7 | — |
|  | Week 4 | 31 | 17.0 ± 7.7 | — | 9.8 ± 5.1** | — |
|  | Week 8 | 30 | 15.1 ± 6.8**# | — | 7.3 ± 4.9**# | — |
|  | Week 12 | 30 | 12.1 ± 10.8**# | 49.2# | 5.5 ± 3.2**# | 56.9# |
|  | Week 16 | 29 | 11.5 ± 6.8** | — | 5.9 ± 3.7** | — |
|  | Week 20 | 28 | 10.3 ± 7.1** | — | 5.4 ± 4.5** | — |
|  | Week 24 | 27 | 8.3 ± 6.0** | 61.1 | 2.9 ± 2.2** | 77.5# |
| Control | Week 0 | 31 | 20.1 ± 8.6 | — | 12.4 ± 5.1 | — |
|  | Week 4 | 31 | 18.6 ± 7.5 | — | 10.2 ± 4.0 | — |
|  | Week 8 | 30 | 17.3 ± 6.8 | — | 10.3 ± 4.9 | — |
|  | Week 12 | 30 | 15.5 ± 5.8 | 19.8 | 10.3 ± 4.8 | 13.9 |
|  | Week 16 | 29 | 13.1 ± 6.2** | — | 6.8 ± 3.3** | — |
|  | Week 16 | 28 | 11.1 ± 6.1** | — | 6.0 ± 4.1** | — |
|  | Week 24 | 27 | 8.7 ± 5.5** | 56.6 | 4.5 ± 3.2** | 58.9 |

**when the experimental data obtained at a designated time point was compared to that obtained at Week 0 in the same test group, $p < 0.01$;
when the experimental data of the experimental group was compared with that of the control group as obtained at the same time point, $p < 0.05$; and
—: not determined.

tures of nail psoriasis, in particular nail bed discoloration, onycholysis and pitting.

TABLE 14

The individual NAPSI scores of the fingernails in the experimental and control groups calculated at the end of Week 12 based on the clinical features of nail psoriasis.

|  |  |  | Number of | NAPSI score (mean ± SD) | |
| --- | --- | --- | --- | --- | --- |
| Clinical feature | | Group | fingernails | Week 0 | Week 12 |
| Nail matrix psoriasis | Pitting | EXP | 69[a] | 2.51 ± 1.12[b] | 1.10 ± 1.33** |
|  |  | Control | 63 | 2.54 ± 1.13 | 1.79 ± 1.50 |
|  | Leukonychia | EXP | 3 | 1.33 ± 0.58 | 0 |
|  |  | Control | 1 | 2.00 | 0 |

TABLE 14-continued

The individual NAPSI scores of the fingernails in the experimental and control groups calculated at the end of Week 12 based on the clinical features of nail psoriasis.

| | | | Number of | NAPSI score (mean ± SD) | |
|---|---|---|---|---|---|
| Clinical feature | | Group | fingernails | Week 0 | Week 12 |
| | Red spots | EXP | 0 | 0 | 0 |
| | in the lunula | Control | 0 | 0 | 0 |
| | Nail plate | EXP | 50 | 2.94 ± 1.20 | 1.02 ± 1.35 |
| | crumbling | Control | 54 | 2.89 ± 1.16 | 1.24 ± 1.59 |
| Nail bed psoriasis | Onycholysis | EXP | 126 | 1.96 ± 0.65 | 0.63 ± 0.86** |
| | | Control | 119 | 1.93 ± 0.59 | 1.33 ± 2.21 |
| | Splinter | EXP | 28 | 1.39 ± 0.79 | 0.50 ± 0.69 |
| | hemorrhages | Control | 21 | 1.33 ± 0.80 | 0.52 ± 0.68 |
| | Subungual | EXP | 50 | 2.76 ± 0.98 | 1.02 ± 1.08 |
| | hyperkeratosis | Control | 49 | 2.71 ± 0.96 | 1.36 ± 1.16 |
| | Nail bed | EXP | 55 | 2.07 ± 1.14 | 0.27 ± 0.60** |
| | discoloration | Control | 49 | 1.92 ± 1.00 | 0.98 ± 0.96 |

[a]The number of fingernails that exhibited a specific clinical feature as indicated.
[b]The individual NAPSI score calculated based on a specific clinical feature as indicated.
**When the experimental data obtained at the end of Week 12 was compared to that of the control group obtained at the end of Week 12, $p < 0.01$.

The overall improvements of nail psoriasis as provided by the indigo naturalis oil drop were further evaluated by a dermatologist and the test subjects at the end of Weeks 12 and 24, and the obtained results are summarized in Table 15.

TABLE 15

The overall improvements of nail psoriasis as evaluated by a dermatologist and the test subjects.

| | Evaluation by test subjects | | | | Evaluation by dermatologist | | | |
|---|---|---|---|---|---|---|---|---|
| | Week 12 | | Week 24 | | Week 12 | | Week 24 | |
| | Control | EXP | Control | EXP | Control | EXP | Control | EXP |
| Disappeared (5[a]) | 0[b] (0%[c]) | 0 (0%) | 2 (7.4%) | 3 (11.1%) | 0 (0%) | 1 (3.3%) | 4 (14.8%) | 7 (25.9%) |
| Nearly disappeared (4) | 1 (3.3%) | 5 (16.7%) | 7 (25.9%) | 11 (40.7%) | 1 (3.3%) | 8 (26.7%) | 3 (11.1%) | 8 (29.6%) |
| Moderately improved (3) | 4 (13.3%) | 11 (36.7%) | 9 (33.3%) | 7 (25.9%) | 4 (13.3%) | 9 (30.0%) | 10 (37.0%) | 5 (18.5%) |
| slightly improved (2) | 6 (20%) | 8 (26.7%) | 6 (22.2%) | 4 (14.8%) | 5 (16.7%) | 8 (26.7%) | 5 (18.5%) | 5 (18.5%) |
| No change (1) | 7 (23.3%) | 4 (13.3%) | 2 (7.4%) | 1 (3.7%) | 11 (36.7%) | 2 (6.7%) | 3 (11.1%) | 0 (0%) |
| Worse (0) | 12 (40%) | 2 (6.7%) | 1 (3.7%) | 1 (3.7%) | 9 (30.0%) | 2 (6.7%) | 2 (7.4%) | 2 (7.4%) |

[a]A ranking score as indicated.
[b]The number of test subjects having a ranking score as indicated.
[c]The percentage of said number of test subjects relative to the total number of test subjects.

It can be seen from Table 15 that not only the dermatologist but also most of the test subjects considered the indigo naturalis oil drop according to this invention to be effective in relieving psoriatic nail lesions. In particular, most of the test subjects considered that their affected fingernails were significantly ameliorated at the end of Week 24 as compared to the overall improvement evaluated at the end of Week 12.

B. Safety Evaluation of the Indigo Naturalis Oil Drop

During the test time, no adverse skin response was observed for all of the fingernails applied with the indigo naturalis oil drop (data not shown).

In view of the aforesaid, the applicants contemplate that the olive oil-extracted product of indigo naturalis according to this invention can be developed into an anti-psoriatic drug for long-term use in treating psoriatic diseases, in particular skin psoriasis and nail psoriasis.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claim.

I claim:

1. An oil-extracted product of indigo naturalis which is obtained by a process comprising extracting indigo naturalis powder with an oil under heating, followed by a refining treatment by filtration, wherein in said process, extracting indigo naturalis powder is conducted at a temperature ranging from 100° C. to 155° C.

2. The oil-extracted product of indigo naturalis as claimed in claim 1, which comprises indirubin.

3. The oil-extracted product of indigo naturalis as claimed in claim 1, wherein in said process, the oil-extracted product obtained after the refining treatment has a decreased indigo content.

4. The oil-extracted product from indigo naturalis as claimed in claim 1, wherein the oil used in said process is selected from the group consisting of vegetable oils, animal oils, mineral oils, and combinations thereof.

5. The oil-extracted product from indigo naturalis as claimed in claim 4, wherein the oil is a vegetable oil selected from the group consisting of olive oil, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, camellia oil, grape seed oil, canola oil, castor oil, and combinations thereof.

6. A pharmaceutical composition comprising an oil-extracted product of indigo naturalis as claimed in claim 1.

7. A method for treating a human subject having or suspected to have a psoriatic disease, comprising treating said human subject with a pharmaceutical composition as claimed in claim 6.

8. The method of claim 7, wherein the psoriatic disease is selected from skin psoriasis, nail psoriasis, chronic plaque psoriasis, guttate psoriasis, erythrodermic psoriasis, pustular psoriasis, and combinations thereof.

9. The method of claim 7, wherein an additional antipsoriatic drug is used to treat said subject.

10. The pharmaceutical composition of claim 6, wherein in said process, the oil-extracted product obtained after the refining treatment has a decreased indigo content.

11. The method of claim 7, wherein in said process, the oil-extracted product obtained after the refining treatment has a decreased indigo content.

12. A process for preparing an oil-extracted product of indigo naturalis, comprising subjecting indigo naturalis powder to an extraction treatment using an oil under heating and subsequent to the extraction treatment, performing a refining treatment by filtration,
wherein the extraction treatment is conducted at a temperature ranging from 100° C. to 155° C.

13. The process of claim 12, wherein the oil used in the extraction treatment is selected from the group consisting of vegetable oils, animal oils, mineral oils, and combinations thereof.

14. The process of claim 13, wherein the oil used in the extraction treatment is a vegetable oil selected from the group consisting of olive oil, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, camellia oil, grape seed oil, canola oil, castor oil, and combinations thereof.

* * * * *